United States Patent [19]

Kim

[11] Patent Number: 4,593,100
[45] Date of Patent: Jun. 3, 1986

[54] 3A,4,7,7A-TETRAHYDRO-3,6,7A-TRIMETHYL-4-SUBSTITUTED PHENYL-ISOXAZOLO[5,4-B]PYRIDINE-5-CARBOXYLIC ACID ESTERS

[75] Inventor: Dong H. Kim, Wayne, Pa.

[73] Assignee: American Home Products Corporation, New York, N.Y.

[21] Appl. No.: 684,884

[22] Filed: Dec. 21, 1984

[51] Int. Cl.$^4$ .......................................... C07D 498/04
[52] U.S. Cl. .................................................. 546/115
[58] Field of Search ........................................ 546/115

[56] References Cited

FOREIGN PATENT DOCUMENTS 59-152386 8/1984 Japan ................................... 546/115

OTHER PUBLICATIONS

Burrows et al., *Journal of the American Chemical Society*, 79, 3756 (1957).

*Primary Examiner*—Henry R. Jiles
*Assistant Examiner*—Bernard I. Dentz

*Attorney, Agent, or Firm*—Arthur G. Seifert

[57] ABSTRACT

Disclosed herein are 4-phenyl-tetrahydro-isoxazolo[5,4-b]-pyridine-5-carboxylic acid esters of Formula I:

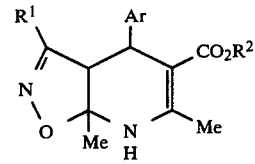

wherein Ar is phenyl or phenyl substituted by a halogen, nitro, or trifluoromethyl group; $R^1$ is $C_{1-3}$ alkyl; and $R^2$ is $C_{1-5}$ alkyl, $(C_{1-5})$ alkoxy $(C_{1-3})$-alkyl, or mono- or di($C_{1-5}$) alkylamino $(C_{1-3})$alkyl;

or physiologically acceptable acid addition salts thereof. The compounds of the invention exhibit calcium antagonist and antihypertensive properties in standard pharmacological procedures.

5 Claims, No Drawings

3A,4,7,7A-TETRAHYDRO-3,6,7A-TRIMETHYL-4-SUBSTITUTED PHENYL-ISOXAZOLO[5,4-B]PYRIDINE-5-CARBOXYLIC ACID ESTERS

This invention concerns 4-phenyl-tetrahydro-isoxazolo[5,4-b]-pyridine-5-carboxylic acid esters of Formula I:

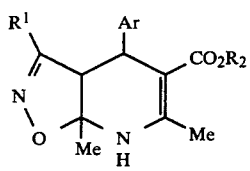

wherein Ar is phenyl or phenyl substituted by a halogen, nitro, or trifluoromethyl group; $R^1$ is $C_{1-3}$ alkyl; and $R^2$ is $C_{1-5}$ alkyl, $(C_{1-5})$ alkoxy $(C_{1-3})$-alkyl, or mono- or di$(C_{1-5})$ alkylamino $(C_{1-3})$ alkyl;
or physiologically acceptable acid addition salts thereof.

The compounds of the invention exhibit calcium antagonist and antihypertensive properties in standard pharmacological procedures.

BACKGROUND OF THE INVENTION

In an article entitled "The Beckman Rearrangement of -Dihydrocembellulone Oxime", *Journal of the American Chemical Society*, 79, 3756 (1957), W. D. Burrows and R. H. Eastman report the synthesis of 4,5,7,7a-tetrahydro-7a-isopropyl-4-methyl isoxazole[5,4-b]-pyridin-6(32H)-one (XIV) by nitrosation of 5-methyl-1-isopropyl-2-azabicyclo[4.1.0]heptanon-3 (V). This reaction is represented as follows:

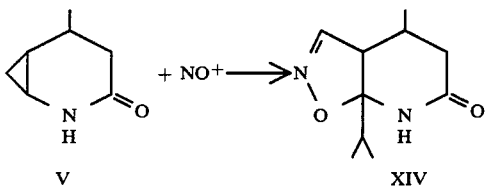

No pharmacological or other utility is noted for the product XIV.

Applicant, on the other hand, has discovered that 3a,4,7,7a-tetrahydro3,6,7a-trimethyl-4-substituted phenylisoxazolo[5,4-b]pyridine-5-carboxylates of Formula I may be obtained by treating the corresponding 5-acetyl-1,4-dihydro-2,6-dimethyl-4-substituted phenyl-3-pyridinecarboxylates of Formula II with hydroxylamine in pyridine. Applicant has further discovered that said isooxazolo[5,4-b]pyridines of Formula I exhibit calcium antagonist and antihypertensive properties as shown in standard pharmacological procedures.

DETAILED DESCRIPTION OF THE INVENTION

As described above in Formula I, Ar may represent a phenyl group or a phenyl group substituted by halogen, nitro, or trifluoromethyl group. "$C_{1-3}$ alkyl" means a lower alkyl group of 1-3 carbon atoms, namely, a methyl, ethyl, propyl, or isopropyl group. "Halogen" means fluorine, chlorine, bromine, or iodine.

$R^1$ may be $C_{1-5}$ alkyl and $R^2$ may be $C_{1-5}$ alkyl, $(C_{1-5})$-alkoxy$(C_{1-3})$alkyl; or mono- or di-$(C_{1-5})$alkylamino-$(C_{1-3})$ alkyl. "$C_{1-5}$ alkyl" means a lower alkyl group of 1-5 carbon atoms, for example, methyl, ethyl, propyl, isopropyl, butyl, isobutyl to butyl, pentyl, isopentyl, etc. "$(C_{1-5})$alkoxy$(C_{1-3})$alkyl" means a lower alkoxy group of 1-5 carbon atoms attached to a straight chain alkyl group of 1-3 carbon atoms, for example, methoxymethyl isopropoxymethyl, ethoxyethyl, butoxypropyl or isopentoxypropyl. "Mono- or di-$(C_{1-5})$alkylaminoalkyl" means a monoalkyl or dialkylamino group, in which the alkyl group has 1-5 carbon atoms, attached to an alkyl group of 1-3 carbon atoms, for example, methylaminomethyl, diethylaminomethyl, di-isopentylaminopropyl, etc. With respect to the above-defined $R^1$ and $R^2$ $C_{1-5}$ alkyl groups, such groups of 1-3 carbon atoms are preferred.

The preparation of the compounds of Formula I of the invention is illustrated by the following reaction scheme:

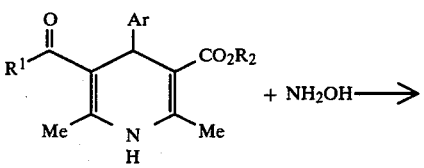

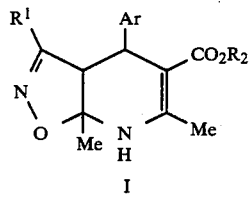

The 5-acetyl-1,4-dihydro-2,6-dimethyl-4-(2-nitrophenyl)-3-pyridinecarboxylic acid ethyl ester starting material (II) used in the present invention has been reported by Berson and Brown (*J. Amer. Chem. Soc.*, 77, 444(1955)) and was prepared as reported therein. The other starting materials of Formula II are prepared according to the method described by them with a minor modification, as shown in Example 1 below.

As shown in the reaction scheme above, the thus obtained 1,4-dihydropyridine starting materials II are treated with hydroxylamine to obtain the final tetrahydro-isoxazolo[5,4-b]pyridine products of Formula I. Preferably, hydroxylamine hydrochloride is used and the reaction is run in a polar solvent, such as ethanol, in the presence of base, such as pyridine.

As described earlier herein, the compounds of the invention exhibit pharmacological activity as $Ca^{2+}$ antagonists. One of the exemplified compounds also exhibits antihypertensive activity in vivo after oral administration.

Pharmacological agents possessing the ability to block cellular transmembrane influx of calcium are capable of suppressing that portion of myocardial or vascular smooth muscle contractility which is dependent upon extracellular calcium. Church et al., *Can. J. Physiol. Pharmacol.*, 58, 254 (1980); Fleckenstein, *Calcium and the Heart*, P. Harris and L. Opie, eds., Academic Press (1971); Nayler et al., *Bas. Res. Cardiol.*, 76, 1 (1980); *Calcium Blockers*, S. Flaim and R. Zelis, eds., Urban and Schwartzenberg, (1982).

The pharmacological agents, termed calcium entry blockers, have been proven to be useful in the treatment of hypertension, cardiac arrhythmias, angina pectoris, and coronary artery vasospasm (a possible cause of sudden cardiac death syndrome). Circ. Res., 52, Suppl. I, (1983); *Hypertension* 5, Suppl. II. (1983).

In theory, calcium entry blockers are thought to act by blocking calcium influx through discrete calcium channels (slow channels) in cell membranes. Various tissues exhibit relative differences in sensitivity toward the calcium blocking effect achieved by certain calcium antagonists, theoretically as a result of tissue specific differences in the calcium channels. *Acta Pharmacol. Toxicol.*, 43, 5 (1978); loc. cit. 291 (1978); *Microvascular Res.*, 5, 73 (1973); *Am. Rev. Pharmacol. Toxicol.*, 17, 149 (1977).

The compounds of this invention were shown to exhibit $Ca^{+2}$ antagonism in rabbit aortic smooth muscle following a modified procedure from that described by Brockaert et al., *Eur. J. Pharmacol.*, 53, 281 (1979) whereby transverse strips (10 mm $\times$ 2.5 mm), from the thoracic aorta were cut and suspended vertically in a jacketed (37° C.-50 ml volume) organ bath in physiological saline solution (PSS) aerated with 95% $O_2$/5% $CO_2$. The composition of PSS was as follows (mM): NaCl 112, KCl 5, $NaHCO_3$ 25, $KH_2PO_4$ 1, $MgSO_4$ 1.2, $CaCl_2$ 2.5, dextrose 10. The lower end of each tissue strip was attached to a fixed post and the upper end to a Statham UC-4 transducer. Changes in force development were recorded on a Beckman Dynograph Polygraphic Recorder. Following equilibration, the muscles were contracted in a depolarizing solution of PSS in which 100 mM KCl was substituted for an equimolar concentration of NaCl. Following attainment of steady-state isometric force (20 min.), the test compound was added to afford a final concentration of $1 \times 10^{-5}$M. The inhibitory effect, expressed as percent relaxation, was determined from the mean of two experiments twenty minutes after the addition of the compound being tested.

When measured according to the above procedure, the compound of Examples 3 produced moderate $Ca^{2+}$ antagonist activity, with a percentage of relaxation of 59%.

The antihypertensive effect of a compound of Formula I is elicited and demonstrated by administering the compound to a hypertensive rat and measuring the change in systolic blood pressures from just prior to drug administration to 1.5, 4, and 24 hours thereafter. The systolic blood pressure of male conscious, spontaneously hypertensive rat (SHR) (Taconic Farms) is measured by indirect tail plethysmography using a system designed and built by Narco Bio-Systems—(-Module MK-IV). Groups consisting of 4 rats receive a single oral dose of the test compound. Rats are warmed in a heated chamber at 38° C. for 10 minutes prior to measurement of systolic pressure to increase the accuracy of the measurements. The systolic pressure and heart rate data are collected in an Hewlett Packard 88 computer. Data are grouped and summarized, with the mean change in pressure and heart rate at each time period calculated.

When measured according to this procedure, the compound of Example 3 produced a decrease in blood pressure of $-19$ mm of Hg after 1.5 hours at an oral dose of 50 mg/kg.

The compounds of Formula I may exist either in the form of the free base or an acid addition salt thereof. Methods of converting the free base to a salt or vice versa are well known in the art. Particular salts may be utilized by the medicinal chemist for purposes of isolating and/or characterizing a compound of Formula I (or an intermediate compound).

For pharmacological and therapeutic use the compounds of Formula I may be used or administered in the free base form or as a physiologically acceptable acid addition salt. The preparation and use of such salts is well known in the art. Examples of appropriate salts are those formed from the following inorganic and organic acids: hydrochloric, hydrobromic, sulfonic, sulfuric, phosphoric, nitric, maleic, fumaric, benzoic, ascorbic, pamoic, succinic, methanesulfonic, acetic, propionic, tartaric, citric, lactic, malic, madelic, cinamic, palmitic, itaconic, and benzenesulfonic.

The invention includes all such acid addition salts of the compounds of Formula I. The physiologically acceptable acid addition salts are preferred.

EXAMPLE 1

5-Acetyl-1,4-Dihydro-2,6-Dimethyl-4-[3-(Trifluoromethyl)Phenyl]-3-Pyridinecarboxylic Acid Ethyl Ester A mixture of 3-trifluoromethylbenzaldehyde (12 g), acetylacetone (6.9 g), and piperidine (15 drops) was stirred at room temperature overnight. The reaction mixture was dissolved in toluene, and the toluene solution was washed with dilute hydrochloric acid, and dried over magnesium sulfate. Evaporation of toluene afforded a thick oily residue. Ethyl 3-aminocrotonate (7.0 g) was added to the residue, and the resulting mixture was heated on a steam bath overnight. The crude product was purified by a preparative HPLC, then recrystallized from toluene to give the titled product (4.1 g), mp 133°-1314.5° C.

Analysis for: $C_{19}H_{20}F_3NO_3$: Calculated: C,62.12;H,5.49;N,3.81. Found: C,62.30;H,5.67;N,4.04.

EXAMPLE 2

3a,4,7,7a-Tetrahydro-3,6,7a-Trimethyl-4-[3-(Trifluoromethyl)-Phenyl]-Isoxazolo[5,4b-]Pyridine-5-Carboxylic Acid Ethyl Ester A mixture of 5-acetyl-1,4-dihydro-2,6-dimethyl-4-[3-trifluoromethyl)phenyl]-3-pyridinecarboxylic acid ethyl ester (2.08 g), hydroxylamine hydrochloride (0.40 g), pyridine (0.43 g), and ethanol (40 mL) was heated on a steam bath for 2 days. Evaporation of the reaction mixture on a rotary evaporator afforded an oil residue. The titled compound (0.32 g) was isolated from the crude product by a preparative HPLC, and purified by recrystallization from toluene, mp 130°-132° C.

Analysis for: $C_{19}H_{21}F_3N_2O_3$: Calculated: C,59.68;H,5.54;N,7.33. Found: C,59.72;H,5.69;N,7.36.

EXAMPLE 3

3a,4,7,7a-Tetrahydro-3,6,7a-Trimethyl-4-(2-Nitrophenyl)-Isoxazolo[5,4-b]Pyridine-5-Carboxylic Acid Ethyl Ester A mixture of 5-acetyl-1,4-dihydro-2,6-dimethyl-4-(2-nitrophenyl)-3-pyridinecarboxylic acid (J. A. Berson and E. Brown, *J. Amer. Chem. Soc.*, 77, 444 (1955), 2.34 g), hydroxylamine hydrochloride (0.71 g), pyridine (0.81 g), and ethanol (50 mL)) was heated under reflux on a steam bath for 4 hours, then evaporated on a rotary evaporator. The residue was dissolved in hot methanol, and the solution was filtered. The filtrate was concentrated on a rotary evaporator, and chilled in an ice-bath to cause a separation of a precipitate. The precipitate was collected on a filter, and recrystallized once more from methanol to give the titled product (0.1 g), mp 211.5°–212.5° C.

Analysis for: $C_{18}H_{21}N_3O_5$: Calculated: C,60.16;H,5.89;N,11.69. Found: C,60.09;H,5.97;N,12.01.

What is claimed is:

1. A compound of the formula:

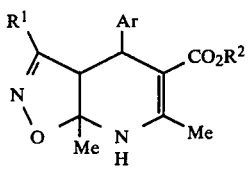

wherein
Ar is phenyl or phenyl substituted by a halogen, nitro, or trifluoromethyl group; $R^1$ is $C_{1-3}$ alkyl; and $R^2$ is $C_{1-5}$ alkyl, ($C_{1-5}$) alkoxy ($C_{1-3}$), or mono- or di($C_{1-5}$) alkylamino ($C_{1-3}$) alkyl;
or physiologically acceptable acid addition salts thereof.

2. A compound of claim 1 in which Ar is chlorophenyl.

3. A compound of claim 1 in which $R^1$ and $R^2$ are, independently, methyl or ethyl.

4. A compound of claim 1 which is 3a,4,7,7a-tetrahydro-3,6,7a-trimethyl-4-[3-(trifluoromethyl)-phenyl]-isoxazolo[5,4-b]pyridine-5-carboxylic acid ethyl ester.

5. A compound of claim 1 which is 3a,4,7,7a-tetrahydro-3,6,7a-trimethyl-4-(2-nitrophenyl)-isoxazolo[5,4-b]pyridine-5-carboxylic acid ethyl ester.

* * * * *